US009435816B2

(12) United States Patent
Johansen et al.

(10) Patent No.: US 9,435,816 B2
(45) Date of Patent: Sep. 6, 2016

(54) DEUTERIUM FREE, STABLE ISOTOPE LABELED 2-PHENYLETHYLAMINE HALLUCINOGENS AND/OR STIMULANTS, METHODS OF THEIR PREPARATION AND THEIR USE

(75) Inventors: Jon Eigill Johansen, Tiller (NO); Huiling Liu, Trondheim (NO); Morten Karlsen, Trondheim (NO)

(73) Assignee: CHIRON AS, Trondheim (NO)

( * ) Notice: Subject to any disclaimer, the term of this patent is extended or adjusted under 35 U.S.C. 154(b) by 124 days.

(21) Appl. No.: 14/235,121

(22) PCT Filed: Jul. 27, 2012

(86) PCT No.: PCT/EP2012/064824
§ 371 (c)(1),
(2), (4) Date: Mar. 12, 2014

(87) PCT Pub. No.: WO2013/014287
PCT Pub. Date: Jan. 31, 2013

(65) Prior Publication Data
US 2014/0227792 A1 Aug. 14, 2014

(30) Foreign Application Priority Data
Jul. 28, 2011 (EP) .................................... 11175719

(51) Int. Cl.
*G01N 33/94* (2006.01)
*C07C 209/32* (2006.01)
*A61K 31/137* (2006.01)
*G01N 33/96* (2006.01)

(52) U.S. Cl.
CPC ........... *G01N 33/946* (2013.01); *A61K 31/137* (2013.01); *C07C 209/325* (2013.01); *G01N 33/94* (2013.01); *G01N 33/96* (2013.01); *G01N 2560/00* (2013.01); *Y10T 436/10* (2015.01); *Y10T 436/173845* (2015.01)

(58) Field of Classification Search
CPC .......... C07C 209/325; G01N 2560/00; G01N 33/48; G01N 33/94; G01N 33/946; G01N 33/96; Y10T 436/10; Y10T 436/13; Y10T 436/17; Y10T 436/173845; Y10T 436/212; Y10T 436/24; Y10T 436/25
USPC ....... 436/8, 56, 63, 106, 111, 140, 161, 173, 436/174, 901; 549/440; 564/411
See application file for complete search history.

(56) References Cited

U.S. PATENT DOCUMENTS

| 8,455,619 | B2 | 6/2013 | Latham |
| 8,703,099 | B2 | 4/2014 | Reis et al. |
| 2005/0014279 | A1* | 1/2005 | Nguyen ............. G01N 33/6848 436/106 |
| 2008/0287774 | A1 | 11/2008 | Katz-Brull |
| 2009/0208413 | A1 | 8/2009 | Reis et al. |
| 2010/0130723 | A1 | 5/2010 | Latham |
| 2012/0156139 | A1 | 6/2012 | Katz-Brull |
| 2013/0177994 | A1* | 7/2013 | Kuntz ................... G01N 33/946 436/111 |

FOREIGN PATENT DOCUMENTS

| JP | 2008266149 A | 11/2008 |
| WO | 2006091885 A1 | 8/2006 |
| WO | 2011024156 A1 | 3/2011 |

OTHER PUBLICATIONS

M. J. Tubergen et al: "Rotational Spectra and Conformational Structures of 1-Phenyl-2-propanol, Methamphetamine, and 1-Phenyl-2-propanone", The Journal of Physical Chemistry A, vol. 110, No. 49, 2006, pp. 13188-13194.
Database Medline [Online] US National Library of Medicine (NLM), Bethesda, MD, US; Oct. 1986, Low I A et al: "Gas chromatographic/mass spectrometric determination of carbon isotope composition in unpurified samples: methamphetamine example.", XP002679720, Database accession No. NLM2947646 & Biomedical & Environmental Mass Spectrometry Oct. 1986 LNKD-PUBMED:2947646, vol. 13, No. 10, Oct. 1986, pp. 531-534, ISSN: 0887-6134.
Mizugaki M et al: "Distribution of carbon-11 labeled methamphetamine and the effect of its chronic administration in mice", Nuclear Medicine and Biology, vol. 20, No. 4, 1993, pp. 487-492.
A.Weisz, S. P. Markey: 'Synthesis of D/L-Norepinephrine-U-13C' Journal of Labelled Compounds and Radiopharmaceuticals vol. XXV, No. 1, pp. 103-109, 1988.
I.A. Low, R.H. Liu, M.G. Legendre, E.G. Piotrowski, R.L. Furner Biomedical & Environmental Mass Spectrometry vol. 13, No. 10, 1986, pp. 531-534.
Collins M et al: "delta(13)C and delta(2)H isotope ratios in amphetamine synthesized from benzaldehyde and nitroethane.", Rapid Communications in Mass Spectrometry, vol. 24, No. 11, Jun. 15, 2010 , pp. 1653-1658.
Cheze et al.: "Simultaneous analysis of six amphetamines and analogues in hair, blood and urine by LC-ESI-MS/MS", Forensic Science International, vol. 170, No. 2-3, 2007, pp. 100-104.
Durso R et al. "Variable absorption of carbidopa affects both peripheral and central levodopa metabolism", Journal of Clinical Pharmacology, vol. 40, No. 8, 2000, pp. 854-860.
Billault et al.: "Correlation between the synthetic origin of methamphetamine samples and their 15N and 13C stable isotope ratios", Analytica Chimica Acta, vol. 593, No. 1, 2007, pp. 20-29.
Shiue C-Y et al. "Fluorine 18 and carbon-11 labeled amphetamine analogs-Synthesis, distribution, binding characteristics, in mice and rats and a PET study in monkey" Nuclear Medicine and Biology, vol. 20, No. 8, 1993, pp. 973-981.

(Continued)

*Primary Examiner* — Maureen Wallenhorst
(74) *Attorney, Agent, or Firm* — Abel Law Group, LLP

(57) ABSTRACT

Deuterium free, stable isotope labeled hallucinogens and/or stimulants containing a 2-phenylethylamine-based structural unit and containing at least three stable isotopes selected from the group consisting of $^{13}$C, $^{15}$N and $^{18}$O as free bases and as their salts; method of their preparation and their use in the chemical analysis, in particular forensic chemical analysis, and in metabolic studies.

19 Claims, No Drawings

(56) References Cited

OTHER PUBLICATIONS

Shiue C-Y et al.: "Comparative PET Studies of the Distribution of (-)-3, 4-Methylenedioxy-N-[<11>C] Methamphetamine in a Monkey Brain", Nuclear Medicine and Biology, vol. 22, No. 3, 1995, pp. 321-324.

Liu et al.: "Peer Reviewed: Isotopically Labeled Analogues for Drug Quantitation", Analytical Chemistry, vol. 74, No. 23, Dec. 1, 2002, pp. 618 A-626 A.

Chang et al.: "13C4-Secobarbital as the Internal Standard for the Quantitative Determination of Secobarbital-A Critical Evaluation", J Forensic Sci, vol. 45, No. 3, Jan. 1, 2000, pp. 659-664.

Ceder et al.: "Concentrations of Unconjugated Morphine, Codeine and 6-Acetylmorphine in Urine Specimens from Suspected Drugged Drivers", Journal of Forensic Sciences, Callaghan and Co, Chicago, IL, US, vol. 47, No. 2, Jan. 1, 2002, pp. 366-368.

Cheze et al.: "Simultaneous analysis of six amptehamines and analogues in hair, blood and urine by LC-ESI-MS/MS Application to the determination of MDMA after low Ecstasy intake", Forensic Science International, Elsevier Scientific Publishers Ireland Ltd, IE, vol. 170, No. 2-3, Jul. 26, 2007, pp. 100-104.

Bjork et al.: "Determination of 19 drugs of abuse and metabolites in while blood by high-performance liquid chromatography-tandem mass spectrometry", Analytical and Bioanalytical Chemistry, Springer, Berlin, DE, vol. 396, No. 7, Nov. 18, 2009, pp. 2393-2401.

Couchman et al.:"LC-MS in analytical toxicology: some practical considerations", Biomedical Chromatography, vol. 25, No. 1-2, Dec. 10, 2010, pp. 100-123.

\* cited by examiner

US 9,435,816 B2

DEUTERIUM FREE, STABLE ISOTOPE LABELED 2-PHENYLETHYLAMINE HALLUCINOGENS AND/OR STIMULANTS, METHODS OF THEIR PREPARATION AND THEIR USE

FIELD OF THE INVENTION

The present invention relates to novel, deuterium free, stable isotope labeled hallucinogens and/or stimulants comprising a 2-phenylethylamine-based structural unit.

Moreover, the present invention relates to a novel method for the preparation of deuterium free, stable isotope labeled hallucinogens and/or stimulants comprising a 2-phenylethylamine-based structural unit.

Additionally, the present invention relates to the use of the deuterium free, stable isotope labeled hallucinogens and/or stimulants comprising a 2-phenylethylamine-based structural unit as standards in the chemical analysis and metabolic studies 2-phenylethylamine hallucinogens and/or stimulants.

CITED DOCUMENTS

The documents cited in the present application are incorporated by reference in their entirety.

DESCRIPTION OF THE PRIOR ART

Chemical analysis of pharmaceuticals and legal and illegal drugs and their metabolites and impurities can be performed by any method applying combinations of gas chromatography (GC), liquid chromatography (LC), ultra performance liquid chromatography (UPLC), mass spectrometry (MC), tandem mass spectrometry (MC/MC) and/or nuclear magnetic resonance spectroscopy (NMR), as for example, GC-MS, GC-MS/MS, LC-MS, LC-MS/MS, UPLC-MS, UPLC-MS/MS, UPLC-MS/MS, LC-NMR and UPLC-NMR.

The internal standards are used to determine the level or quantity of each analyte in the sample. Traditionally, such an analysis is performed using deuterium labeling of the analyte. However, disadvantages associated with deuterium labeling are the risk of exchange, i.e. deuterium and hydrogen can be exchanged in the workup procedure, and different elution times, i.e. the deuterium labeled compounds elute differently from the native, unlabeled compounds both in GC and in LC. In addition, the deuterium labeled compounds may have a response factor which is slightly different from the response factor of the native, unlabeled compounds. The internal standards are particularly suitable of minimizing the effects of ion suppression effects in LC-MS/MS analysis, therefore the quantitative analysis in various biological samples are particularly accurate and reproducible.

In a $^{13}$C labeled compound, there is no risk of exchange, and the labeled compounds elute identically with the unlabeled compounds both in GC and LC. Moreover, they have the same response factor when using mass detection. However, natural matter contains approximately 1.1% $^{13}$C so that there is a danger of an "overlap" with the natural $^{13}$C in the native compound. Therefore, the number of labeled atoms must preferably be at least three. Further, any labeling of a compound with $^{13}$C, $^{15}$N and/or $^{18}$O and deuterium will lead to a shift in retention time and response factors.

Due to the fragmentation pattern of phenethylamine derivatives (like trifluoroacetic acid (TFA)-derivatives), it is highly desirable that the labeling be in the aromatic ring of the systems.

$^{13}$C labeling has long been used in chemical analysis and in other fields like environmental analysis, in particular in the analysis of trace compounds like dioxins or polychlorinated biphenyls (PCBs). However, no such $^{13}$C labeled compounds have been reported that can be used as chemical standards in order to obtain all the advantages of a compound with pure $^{13}$C labeling not in combination with deuterium labeling.

Therefore, it would be highly desirable to have compounds available that are labeled with $^{13}$C, $^{15}$N and/or $^{18}$O, however, not in combination with deuterium.

In the past years, the abusive use of illegal drugs, in particular 2-phenylethylamine hallucinogens or psychotomimetika, has become a worldwide major concern and has a tremendous negative social, criminal and economical impact in all societies. In particular, the highly addictive 2-phenylethylamine hallucinogens and/or stimulants such as amphetamine, methamphetamine and ecstasy are consumed in ever-growing amounts. Therefore, it would be particularly desirable to have compounds of this type available that are labeled with $^{13}$C, $^{15}$N and/or $^{18}$O, however, not in combination with deuterium, in order to have reliable standards for the chemical analysis of such illegal psychotropic drugs at hand.

Sigma-Aldrich and Cambridge Isotope Laboratories offer [$^{13}$C$_9$$^{15}$N]-phenylalanine, Cambridge Isotope Laboratories offers [$^{13}$C$_9$]-phenylalanine and [$^{13}$C$_6$]-, [$^{13}$C$_9$]- and [$^{13}$C$_9$$^{15}$N]-tyrosine and Sigma-Aldrich offers [$^{13}$C$_6$]-ritalinic acid. The compounds are used for tandem MS standards. However, the compounds contain carboxylic acid groups and are no hallucinogens and/or stimulants containing a 2-phenylethylamine-based structural unit, Therefore, they cannot serve as a standards for the chemical analysis of the said hallucinogens and/or stimulants.

The Japanese patent application JP 2008-266149 A discloses estradiol with a [$^{13}$CO$_6$]-benzene ring and various [$^{13}$C$_6$]-precursors such as [$^{13}$C$_6$]-benzene, -nitrobenzene, -iodonitrobenzene, -iodoanaline, -iodophenol and -iodoanisol. However, [$^{13}$C$_6$]-estradiol is no hallucinogen containing a 2-phenylethylamine-based structural unit. Therefore, it cannot serve as a standard for the chemical analysis of the said hallucinogens and/or stimulants.

The article by A. Weis and S. P. Markey "Synthesis of D/L-Norepinephrine-U-$^{13}$C)" in Journal of Labelled Compounds and Radiopharmaceuticals, volume XXV, No. 1, pages 103 to 109 describe the synthesis of the said compound. However, norepinephrine is not a hallucinogen containing a 2-phenylethylamine-based structural unit but a hormone and a neurotransmitter and, therefore, cannot serve as a standard for the chemical analysis of the said hallucinogens and/or stimulants.

The international patent application WO 2006/091885 A2 discloses labeled amphetamines, wherein at least one of the atoms are present as deuterium, $^{13}$C or $^{15}$N. Specifically, $^{13}$C-amphetamine, $^{13}$C-methamphetamine, $^{15}$N-amphetamine, $^{15}$N-methamphetamine, $^{13}$C-$^{15}$N-amphetamine and $^{13}$C-$^{15}$N-methamphetamine are disclosed. The compounds are used for a registry method and control system for DEA schedule II-V medicines. Moreover, the international patent application discloses [$^{13}$C$_6$]-methylphenidate (Ritalin™) and its [$^{13}$C$_6$]-precursors. However, this compound is not a hallucinogen.

The international patent application WO 2011/024156 A1 discloses isotopically labeled neurochemical agents such as deuterium labeled amphetamine containing one $^{13}$C-carbon and their use for diagnosing conditions and disorders in medicine.

In the article of M. J. Tubergen, R. J Lavrich, D. F. Plusquellic, and R. D. Suenram in Journal of Physical Chemistry A (2006), 110 (49), 13188-13194, the use of a compound containing 15N labeling in conformal spectroscopic analysis is described.

In the article of I. A. Low, R. H. Liu, M. G. Legendre, E. G. Piotrowski and R. L. Furner in Biomedical & Environmental Mass Spectrometry (1986), 13 (10), 531-534, the use of a methamphetamine containing only one $^{13}$C-carbon atom is described in the mass spectrometry analysis.

OBJECTS OF THE INVENTION

It has been the object of the present invention to provide novel, deuterium free, stable isotope labeled compounds which do not exhibit the disadvantages of the prior art but do not overlap with the isotope level in the unlabeled natural compounds, show in LC and GC the same or essentially the same elution and retention times and response factors as the natural compounds or analytes and are not prone to isotopical exchange during workup procedures. Thus, they should be most advantageously suitable as standards, in particular internal standards for the chemical analysis, in particular the forensic analysis of hallucinogens and/or stimulants containing a 2-phenylethylamine-based structural unit as analytes.

Moreover, it was the object of the invention to provide a novel method for the synthesis of deuterium free, stable isotope labeled hallucinogens and/or stimulants containing a 2-phenylethylamine-based structural unit, which compounds can most advantageously used for the purposes set out above.

Additionally, it was the object of the invention to provide the use of the novel, deuterium free, stable isotope labeled hallucinogens and/or stimulants containing a 2-phenylethylamine-based based structural unit and the compounds prepared by the novel method as standards and chemical analysis in metabolic studies, in particular as internal standards in the forensic analysis of hallucinogens and/or stimulants containing a 2-phenylethylamine-based structural unit.

SUMMARY OF THE INVENTION

Accordingly, novel, deuterium free, stable isotope labeled hallucinogens and/or stimulants containing a 2-phenylethylamine-based structural unit and containing at least three stable isotopes selected from the group consisting of $^{13}$C, $^{15}$N and $^{18}$O as free bases and as their salts have been found, which compounds are hereinafter referred to as the "compounds of the invention".

Moreover, the novel method for preparing deuterium free, stable isotope labeled hallucinogens and/or stimulants containing a 2-phenylethylamine-based structural unit and containing at least three stable isotopes selected from the group consisting of $^{13}$C, $^{15}$N and $^{18}$O as free bases and as their salts has been found, the said method comprising the steps of (1) reacting [$^{13}$C$_6$]-benzaldehyde or a substituted [$^{13}$C$_6$]-benzaldehyde with a nitro group containing compound of the general formula II:

$$O_2N-CH_2-R^3 \qquad (II),$$

to obtain a substituted or unsubstituted nitro compound of the general formula (III) as an intermediate:

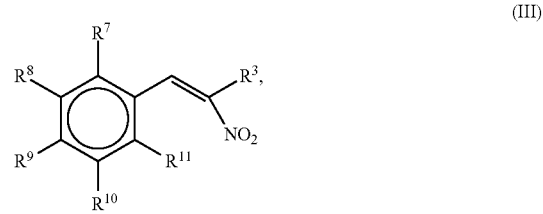

wherein the variables $R^3$, $R^7$, $R^8$, $R^9$, $R^{10}$, and $R^{11}$ are hereinafter defined;

(2) reducing the nitro group and hydrogenating the olefinic double bond of the intermediate III to obtain a 2-phenylethylamine alkaloid or a hallucinogen of the general formula I, wherein the variables $R^1$, $R^2$, $R^3$, $R^4$, $R^5$ and $R^6$ are hydrogen atoms.

Hereinafter, the novel method for preparing deuterium free, stable isotope labeled hallucinogens and/or stimulants containing a 2-phenylethylamine-based structural unit and containing at least three stable isotopes selected from the group consisting of $^{13}$C, $^{15}$N and $^{18}$O as free bases and as their salts is referred to as the "method of the invention".

Additionally, the novel use of the compounds of the invention and of the compounds prepared in accordance with the method of the invention as standards for the chemical analysis and metabolic studies of hallucinogens and/or stimulants containing a 2-phenylethylamine-based structural unit has been found, which use is these hereinafter referred to as the "use of the invention".

Advantages of the Invention

In view of the prior art discussed above, it was surprising and could not be expected by the skilled artisan that the objects underlying the present invention could be solved by the compounds of the invention, the method of the invention and the use of the invention.

In particular, it was surprising that the compounds of the invention did not exhibit the disadvantages of the prior art and did not overlap with the isotope level in the unlabeled natural compounds, showed in LC and GC the same or essentially the same elution and retention times and response factors as the non-labeled compounds or analytes and were not prone to isotopical exchange during workup procedures. Thus, they were most advantageously suitable as standards, in particular internal standards for the chemical analysis, in particular the forensic analysis of hallucinogens and/or stimulants containing at a 2-phenylethylamine-based structural unit as analytes.

Moreover, the method of the invention yielded compounds that could be most advantageously used for the purposes set out above.

Additionally, according to the use of the invention, the compounds of the invention and the deuterium free, stable isotope labeled hallucinogens and/or stimulants containing a 2-phenylethylamine-based structural unit prepared in accordance with the method of the invention could be most advantageously used as standards in chemical analysis and metabolic studies, in particular as internal standards in the forensic analysis of non-labeled hallucinogens and/or stimulants containing a 2-phenylethylamine-based structural unit.

DETAILED DESCRIPTION OF THE INVENTION

In its broadest aspect to present invention is directed to the compounds of the invention.

The compounds of the invention are synthetic and natural hallucinogens and/or stimulants comprising a 2-phenylethylamine-based structural unit. The synthetic hallucinogens and/or stimulants are frequently referred to as "designer drugs". Virtually all of them are highly addictive and, therefore, are prone to drug abuse.

In the context of the present invention "2-phenylethylamine-based structural unit" means that the said structural unit is formally derived from 2-phenylethane amine.

The compounds of the invention are free of deuterium. In the context of the present invention, this means that they contain at the most only the natural level of the deuterium isotope, i.e. 0.015 mol-% of the hydrogen present.

In accordance with the invention, the compounds of the invention comprise at least three stable isotopes selected from the group consisting of $^{13}C$, $^{15}N$ and $^{18}O$, preferably at least three $^{13}C$ isotopes, more preferably at least four $^{13}C$ isotopes, even more preferably at least five $^{13}C$ isotopes, and most preferably six $^{13}C$ isotopes.

Preferably, the at least three $^{13}C$ isotopes are located in the phenyl residue of the 2-phenylethylamine-based structural unit.

More preferably, the compounds of the invention have the general formula I:

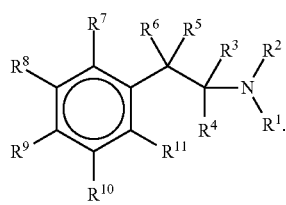

(I)

In the general formula I the variables $R^1$ and $R^2$ designate independently of each other a hydrogen atom or a residue selected from the group consisting of
- organic residues consisting of saturated or unsaturated, substituted or unsubstituted alkyl, cycloalkyl, aryl, alkylcycloalkyl, alkylaryl, cycloalkylaryl or alkylcycloalkylaryl groups containing or not containing at least one heteroatom; and
- organic residues containing at least two different groups selected from saturated and unsaturated, substituted and unsubstituted alkyl, cycloalkyl, aryl, alkylcycloalkyl, alkylaryl, cycloalkylaryl and alkylcycloalkylaryl groups containing or not containing at least one heteroatom.

Examples of suitable saturated alkyl groups $R^1$ and $R^2$ are unbranched or branched alkyl groups comprising 1 to 20 carbon atoms, such as methyl, ethyl, propyl, isopropyl, butyl, isobutyl, tert.-butyl and alkyl groups derived from pentane, hexane, heptane, octane, nonane, undecane, undecane, dodecane, tridecane, tetradecane, pentadecane, hexadecane, heptadecane, octadecane, nonadecane and eicosane and their stereoisomers, as for example, n-pentyl, isopentyl, neopentyl, n-hexyl, n-heptyl, n-octyl, 2,2-dimethylhexyl, 3-methyl-2-ethyl-pentyl, nonyl, decyl, 5-methyl-nonyl, undecyl and dodecyl.

Examples of suitable unsaturated alkyl groups $R^1$ and $R^2$ are branched or unbranched alkylene groups containing 2 to 20 carbon atoms, such as ethenyl and ethynyl groups and ethylenically and acetylenically unsaturated alkyl groups derived from propane, butane, pentane, hexane, heptane, octane, nonane, undecane, undecane, dodecane, tridecane, tetradecane, pentadecane, hexadecane, heptadecane, octadecane, nonadecane and eicosane and their stereoisomers, comprising at least one olefinic double bond and/or acetylenic triple bond, as for example, propene, propyne, n-but-1-ene, n-but-1-yne, butadiene or isoprene.

Examples of suitable saturated cycloalkyl groups $R^1$ and $R^2$ are cyclopentyl and cyclohexyl and groups derived from monocyclic, dicyclic, triyclic or tetracyclic cycloalkanes containing 6 to 16 carbon atoms, such as bicyclo[3.2.1]octane, bicyclo[4.3.2]undecane, decaline, hydrindane or adamantane.

Examples of suitable unsaturated cycloalkyl groups $R^1$ and $R^2$ are cyclopenentyl, cyclohexenyl and norbonenyl groups.

Examples of suitable aryl groups $R^1$ and $R^2$ are phenyl and groups derived from polycyclic aromatic compounds, such as naphthalene, biphenyl or anthracene.

Suitable saturated alkylcycloalkyl groups residues $R^1$ and $R^2$ are derived from monocyclic, dicyclic, triyclic or tetracyclic alkyl substituted cycloalkanes containing 6 to 16 carbon atoms, such as, methylcyclopentane methylcyclohexane, norcamphane, pinane camphane, 10-norbornane, o-menthane, m-menthane, p-menthane, thujane, carane, 2-ethyl-pinane, 2,4,7,7-tetramethylnorcarane, norbonane, 2,2-dimethylnorbornane.

Suitable unsaturated alkylcycloalkyl groups $R^1$ and $R^2$ are derived from monocyclic, dicyclic, triyclic or tetracyclic alkyl substituted cycloalkanes containing 6 to 16 carbon and at least one of ethylenically unsaturated double bond, such as methyl cyclopentene, methyl cyclohexene and monocyclic terpenes, such as alpha- and gamma-terpinene, terpinolene, alpha- and beta-phellandrene or limonene. The unsaturated alkylcycloalkyl groups can be linked to the nitrogen atom via a ring carbon or a carbon of the alkyl group.

Suitable saturated alkylaryl groups $R^1$ and $R^2$ are derived from alkyl substituted benzenes, such as toluene, xylene, propyl benzene, isopropyl benzene, n-butyl benzene, sec-butyl benzene and tert-butyl benzene. The saturated alkylaryl groups can be linked to the nitrogen atom via a ring carbon or via a carbon of the alkyl group.

Examples of suitable unsaturated alkylaryl groups $R^1$ and $R^2$ are styrene and alpha-methyl styrene. The unsaturated alkylaryl groups can be linked to the nitrogen atom via a ring carbon or via a carbon of the alkenyl group.

The saturated and unsaturated alkylcycloalkylaryl groups $R^1$ and $R^2$ consist of at least one saturated or unsaturated alkyl group $R^1$ and $R^2$, at least one saturated or unsaturated cycloalkyl group $R^1$ and $R^2$ and at least one aryl group $R^1$ and $R^2$ as described above, which groups are linked together via at least one carbon-carbon atom bond. The said groups $R^1$ and $R^2$ can be linked to the nitrogen atom via an aromatic ring carbon atom, a cycloaliphatic ring carbon atom or a carbon atom of the alkyl group.

Examples for suitable alkylcycloalkylaryl groups $R^1$ and $R^2$ are 2-cyclohexyl toluene or 1-phenyl-4-methyl cyclohexane.

The saturated and unsaturated organic residues $R^1$ and $R^2$ containing at least two different groups selected from saturated and unsaturated, substituted and unsubstituted alkyl, cycloalkyl, aryl, alkylcycloalkyl, alkylaryl, cycloalkylaryl and alkylcycloalkylaryl groups $R^1$ and $R^2$ comprise at least two of the said groups linked together by at least one bivalent linking group. Examples of suitable bivalent linking groups are:

—O—, —C(O)—, —C(S)—, —C(O)—O—, —O—C(O)—O—, —O—C(S)—O—;
—NR$^1$—, =N—, —N=N—, —NR$^1$—C(O)—, —NR$^1$—NR$^1$—C(O)—, —NR$^1$—NR$^1$—C(S)—, —O—C(O)—NR$^1$—,
—O—C(S)—NR$^1$—, —NR$^1$—C(O)—NR$^1$—, —NR$^1$—C(S)—NR$^1$—;
—S—, —S(O)—, —S(O)$_2$—, —O—S(O)$_2$—, and —NR$^1$—S(O)$_2$—, wherein the residue $R^1$ has the above-described meaning.

The above mentioned groups $R^1$ and $R^2$ can be substituted. Preferably, the substituents are selected from the group consisting of hydroxy groups, primary, secondary and tertiary amino groups, nitrile groups and fluorine, chlorine, bromine and iodine atoms.

More preferably, the groups $R^1$ and $R^2$ are unsubstituted.

Most preferably, the groups $R^1$ and $R^2$ are hydrogen atoms and/or methyl groups.

In the general formula I, the variables $R^3$ and $R^4$ taken together as well as $R^5$ and $R^6$ taken together can be a carbonyl oxygen atom or substituted or unsubstituted imino groups. The above-described organic residues $R^1$ and $R^2$ are suitable substitutes for the substituted imino groups.

The variables $R^3$, $R^4$, $R^5$, $R^6$, $R^7$, $R^8$, $R^9$, $R^{10}$ and $R^{11}$ designate independently of each other hydrogen atoms, hydroxy groups, amino groups, mercapto groups, nitrile groups fluorine atoms, chlorine atoms, bromine atoms, iodine atoms or the above described organic residues $R^1$ and $R^2$.

The organic residues $R^1$, $R^2$, $R^3$, $R^4$, $R^5$, $R^6$, $R^7$, $R^8$, $R^9$, $R^{10}$ and $R^{11}$ may contain heteroatoms. Preferably, the heteroatoms are selected from the group consisting of nitrogen, oxygen and sulfur.

The organic residues $R^3$, $R^4$, $R^5$, $R^6$, $R^7$, $R^8$, $R^9$, $R^{10}$ and $R^{11}$ may also be bonded to the 2-phenylethylamine-based structural unit of the general formula I via an above-described bivalent linking group.

Moreover, at least two of the organic residues $R^1 R^3$, $R^4$, $R^5$, $R^6$, $R^7$, $R^8$, $R^9$, $R^{10}$ and $R^{11}$, in particular $R^1$ and $R^3$, $R^7$ and $R^8$, $R^8$ and $R^9$, $R^9$ and $R^{10}$ and/or $R^{11}$, most particular $R^8$ and $R^9$ may be bonded to each other via a bivalent bridging group.

Suitable bivalent bridging groups are preferably derived from the above-described organic residues $R^1$ and $R^2$ except that they are bivalent and not monovalent. Most preferably, the bivalent bridging groups are methylene groups, —CH$_2$—, —and saturated and unsaturated ethanediyl groups, —CH$_2$—CH$_2$—, —CH=CH— or =CH—CH=.

Preferably, the compounds of the invention are selected from the group consisting of amphetamine, methamphetamine, 3,4-methylenedioxyamphetamine, 3,4-methylenedioxy-N-methylamphetamine, 3,4-methylenedioxy-N-ethylamphetamine, 3-methoxy-4,5-methylenedioxyamphetamine, 2,5-dimethoxy-4-methylamphetamine, macromerine, normacromerine, cathinone, cathine, methcathinone, ethcatinone, mephedrone (2-methylamino-1(4-methylphenyl)propan-1-one), 1-(2-fluorophenyl)-2-methylaminopropan-1-one, 1-(3-fluorophenyl)-2-methylaminopropan-1-one, 1-(4-fluorophenyl)-2-methylaminopropan-1-one, 2-methylamphetamine, 3-methylamphetamine, 4-methylamphetamine, 2-methylmethamphetamine, 3-methylmethamphetamine, 4-methylmethamphetamine, 2-methoxyamphetamine, 3-methoxyamphetamine, 4-methoxyamphetamine, 2-methoxymethamphetamine, 3-methoxymethamphetamine, 4-methoxymethamphetamine, 2-fluoroamphethamine, 3-fluoroamphethamine, 4-fluoroamphethamine, 2-fluoromethamphethamine, 3-fluoromethamphethamine, 4-fluoromethamphethamine, 3,4,5-trimethoxy-2-methylamphetamine, 2,4,5-, 3,4,5-, 2,3,4- 2,3,5-, 2,3,6- and 2,4,6-trimethoxyamphetamine; 2,4,5-, 3,4,5-, 2,3,4- 2,3,5-, 2,3,6- and 2,4,6-trimethoxyphenylethylamine, 2,5-dimethoxy-4-amyl-, 2,5-dimethoxy-4-bromo-, 2,5-dimethoxy-4-butyl-, 2,5-dimethoxy-4-chloro-, 2,5-dimethoxy-4-ethyl-, 2,5-dimethoxy-4-fluoro-, 2,5-dimethoxy-4-(2-fluoroethyl)-2,5-dimethoxy-4-iodo-, 2,5-dimethoxy-4-methyl-, 2,5-dimethoxy-4-nitro-, 2,5-dimethoxy-4-trifluoromethyl-, 2,5-dimethoxy-4-ethoxy-, 2,5-dimethoxy-4-methylthio-, 2,5-dimethoxy-4-ethylthio-, 2,5-dimethoxy-4-isopropylthio-, 2,5-dimethoxy-4-phenylthio- and 2,5-dimethoxy-4-propylthioamphetamine; 2,5-dimethoxy-3,4-dimethyl-, 2,5-dimethoxy-3,4-prop-1,3-ylen-, 2,5-dimethoxy-3,4-but-1,4-ylen, 2,5-dimethoxy-3-isopropyoxy-, 2,5-dimethoxy-3-propyl-, 2,5-dimethoxy-methylseleno-, 2,5-dimethoxy-propylthio-, 2,5-dimethoxy-3-cyclopropylmethylthio-, 2,5-dimethoxy-3-n-butylthio-, 2,5-dimethoxy-3-(2-methoxyeth-1-yl)thio-, 2,5-dimethoxy-3-cyclopropylthio-, 2,5-dimethoxy-3-(1-methyl-prop-1-yl)thio-, 2,5-dimethoxy-3-(2-fluoroeth-1-yl)thioamphetamine; 2-(4-bromo-2,5-dimethoxyphenyl)ethanamine, 1-(4-chloro-2,5-dimethoxyphenyl)-2-aminoethane, 1-(2,5-dimethoxy-4-methylphenyl)-2-aminoethane, 1-(2,5d-4-ethylphenyl)-2-aminoethane, 2-(4-fluoro-2,5-dimethoxyphenyl)-1-aminoethane, 3,4-dimethyl-2,5-dimethoxyphenethylamine, 5-(2-aminoethyl)-4,7-dimethoxyindane, 1,2,3,4-tetrahydro-5,8-dimethoxy-1,4-methanonaphthalene-6-ethanamine, 1,4-dimethoxy-2-naphthaleneethanamine, 2-(2,5-dimethoxyphenyl)ethanamine, 2,5-dimethoxy-4-iodophenethylamine, 2,5-dimethoxy-4-nitrophenethylamine, 2-(2,4,5-trimethoxyphenyl)ethanamine, 2-(4-isopropoxy-2,5-dimethoxyphenyl)ethanamine, 2-(2,5-dimethoxy-4-propylphenyl)ethanamine, 2-(2,5-dimethoxy-4-(methylthio)phenyl)ethanamine, 2-[4-(ethylthio)-2,5-dimethoxyphenyl]ethanamine, 2-[4-(isopropylthio)-2,5-dimethoxyphenyl]ethanamine, 2-[2,5-dimethoxy-4-(propylthio)phenyl]ethanamine, 2-[4-[(cyclopropylmethyl)thio]-2,5-dimethoxyphenyl]ethanamine, 2-[4-(butylthio)-2,5-dimethoxyphenyl]ethanamine, 2-[4-(methoxyethylthio)-2,5-dimethoxyphenyl]ethanamine, 2-[4-(cyclopropylthio)-2,5-dimethoxyphenyl]ethanamine, 2-[4-(isobutylthio)-2,5-dimethoxyphenyl]ethanamine, 2-[2,5-dimethoxy-4-(2-fluoroethylthio)phenyl]ethanamine, 2,5-dimethoxy-4-(trifluoromethyl)phenethylamine, 1-amino-2-(1,4-naphth-2-yl)amphetamine, 3,6-dimethoxy-5-ethylthioamphetamine, 4-methyl-5-phenyl-2-amino-oxazoline (4-methylaminorex); 5-phenyl-2-amino-oxazoline (aminorex), 2,5-dimethoxy-3,4-methylenedioxyamphethamine (DMMDA). in particular amphetamine, methamphetamine, 3,4-methylenedioxyamphetamine, and 3,4-methylenedioxy-N-ethylamphetamine (ecstasy).

More preferably, the compounds of the invention are selected from the group consisting of [$^{13}C_6$]-amphetamine, -methamphetamine, -3,4-methylenedioxyamphetamine, -3,4-methylenedioxy-N-methylamphetamine, -3,4-methylenedioxy-N-ethylamphetamine, -3-methoxy-4,5-methylenedioxyamphetamine, -2,5-dimethoxy-4-methylamphetamine, -macromerine, -normacromerine, -cathinone, -cathine, -methcathinone, -ethcatinone, mephedrone-(2-methylamino-1(4-methylphenyl)propan-1-one), -1-(2-fluorophenyl)-2-methylaminopropan-1-one, -1-(3-fluorophenyl)-2- methylaminopropan-1-one, -1-(4-fluorophenyl)-2-methylaminopropan-1-one, -2-methylamphetamine, -3-methylamphetamine, -4-methylamphetamine, 2-methylmethamphetamine, -3-methylmethamphetamine, -4-methylmethamphetamine, -2-fluoroamphethamine, -3-fluoroamphethamine, -4-fluoroamphethamine, -2-fluoromethamphethamine, -3-fluoromethamphethamine, -[4-fluoromethamphethamine, -3,4,5-trimethoxy-2-methylamphetamine, -2,4,5-, -3,4,5-, -2,3,4- 2,3,5-, -2,3,6- and -2,4,6-trimethoxyamphetamine; -2,4,5-, -3,4,5-, -2,3,4- 2,3, 5-, -2,3,6- and -2,4,6-trimethoxyphenylethylamine, -2,5-dimethoxy-4-amyl-, -2,5-dimethoxy-4-bromo-, -2,5-dimethoxy-4-butyl-, 2,5-dimethoxy-4-chloro-, -2,5-dimethoxy-4-ethyl-, -2,5-dimethoxy-4-fluoro-, -2,5-dimethoxy-4-(2-fluoroethyl)-, -2,5-dimethoxy-4-iodo-, -2,5-dimethoxy-4-methyl-, -2,5-dimethoxy-4-nitro-, -2,5-dimethoxy-4-trifluoromethyl-, -2,5-dimethoxy-4-ethoxy-, -2,5-dimethoxy-4-methylthio-, -2,5-dimethoxy-4-ethylthio-, -2,5-dimethoxy-4-isopropylthio-, -2,5-dimethoxy-4-phenylthio- and -2,5-dimethoxy-4-propylthioamphetamine; -2,5-dimethoxy-3,4-dimethyl-, -2,5-dimethoxy-3,4-prop-1,3-ylen-, -2,5-dimethoxy-3,4-but-1,4-ylen, -2,5-dimethoxy-3-isopropyoxy-, -2,5-dimethoxy-3-propyl-, -2,5-dimethoxymethylseleno-, -2,5-dimethoxy-propylthio-, -2,5-dimethoxy-3-cyclopropylmethylthio-, -2,5-dimethoxy-3-n-butylthio-, -2,5-dimethoxy-3-(2-methoxyeth-1-yl)thio-, -2,5-dimethoxy-3-cyclopropylthio-, -2,5-dimethoxy-3-(1-methyl-prop-1-yl)thio- and -2,5-dimethoxy-3-(2-fluoroeth-1-yl)thioamphetamine; -1-amino-2-(1,4-naphth-2-yl)ethane, -3,6-dimethoxy-5-ethylthioamphetamine, -2-(4-bromo-2,5-dimethoxyphenyl)ethanamine, -1-(4-Chloro-2,5-dimethoxyphenyl)-2-aminoethane, -1-(2,5-dimethoxy-4-methylphenyl)-2-aminoethane, -1-(2,5-dimethoxy-4-ethylphenyl)-2-aminoethane, -2-(4-fluoro-2,5-dimethoxyphenyl)-1-aminoethane, -3,4-dimethyl-2,5-dimethoxyphenethylamine, -5-(2-aminoethyl)-4,7-dimethoxyindane, -1,2,3,4-tetrahydro-5,8-dimethoxy-1,4-methanonaphthalene-6-ethanamine, -1,4-dimethoxy-2-naphthaleneethanamine, -2-(2,5-dimethoxyphenyl)ethanamine, -2,5-dimethoxy-4-iodophenethylamine, 2,5-dimethoxy-4-nitrophenethylamine, -2-(2,4,5-trimethoxyphenyl)ethanamine, -2-(4-Isopropoxy-2,5-dimethoxyphenyl)ethanamine, -2-(2,5-dimethoxy-4-propylphenyl)ethanamine, -2-(2,5-dimethoxy-4-(methylthio)phenyl)ethanamine, -2-[4-(ethylthio)-2,5-dimethoxyphenyl]ethanamine, -2-[4-(isopropylthio)-2,5-dimethoxyphenyl]ethanamine, -2-[2,5-dimethoxy-4-(propylthio)phenyl]ethanamine, -2-[4-[(cyclopropylmethyl)thio]-2,5-dimethoxyphenyl]ethanamine, -2-[4-(butylthio)-2,5-dimethoxyphenyl]ethanamine, -2-[4-(methoxyethylthio)-2,5-dimethoxyphenyl]ethanamine, -2-[4-(cyclopropylthio)-2,5-dimethoxyphenyl]ethanamine, -2-[4-(isobutylthio)-2,5-dimethoxyphenyl]ethanamine, -2-[2,5-dimethoxy-4-(2-fluoroethylthio)phenyl]ethanamine, -2,5-dimethoxy-4-(trifluoromethylthio)phenethylamine, -5-phenyl-2-aminooxazoline (-aminorex) and 4-methyl-5-phenyl-2-aminooxazoline (-4-methylaminorex), and -2,5-dimethoxy-3,4-methylenedioxyamphethamine (DMMDA); in particular $[^{13}C_6]$-amphetamine, $[^{13}C_6]$-methamphetamine, $[^{13}C_6]$-3,4-methylenedioxyamphethamine, $[^{13}C_6]$-3,4-methylenedioxy-N-ethylamphetamine (ecstasy) and $[^{13}C_6]$-3,4-methylenedioxy-N-methylamphetamine.

The compounds of the invention can be the free bases or their salts, in particular the salts with inorganic acids such as hydrofluoric acid, HCl, hydrobromic acid, hydroiodic acid, perchloric acid, sulfuric acid, sulfurous acid, phosphoric acid, and phosphonic acid; and organic acids such as carboxylic acids, sulfonic acids, acidic sulfuric acid esters, phosphonic acids and acidic phosphoric acid esters, in particular particularly formic acid, acetic acid, trifluoroacetic acid, propionic acid, trifluorosulfonic acid, citric acid, fumaric acid, and oxalic acid.

The compounds of the invention can have D-, L- and DL-forms ((S)-, (R)- and (RS)-forms).

The compounds of the invention can be prepared by methods of the organic synthesis which are customary and known for the synthesis of hallucinogens and/or stimulants containing at least one, preferably one 2-phenylethylamine-based structural unit from precursors containing the desired number of the desired stable isotopes.

Preferably, the compounds of the invention are prepared by the method of the invention.

In the first process step of the method of the invention, $[^{13}C_6]$-benzaldehyde or substituted $[^{13}C_6]$-benzaldehyde is reacted with a compound of the general formula II:

$$O_2N-CH_2-R^3 \qquad (II),$$

to obtain a substituted or unsubstituted intermediate of the general formula III:

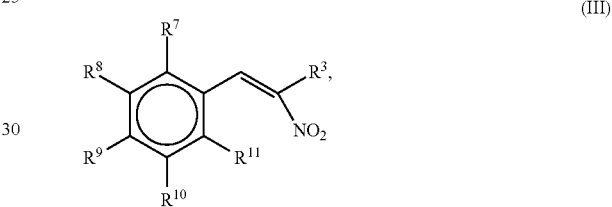

(III)

wherein the variables $R^3$ can be hydrogen, methyl, ethyl, propyl, butyl or other alkyl, preferably linear and, $R^7$, $R^8$, $R^9$, $R^{10}$ and $R^{11}$ have the aforementioned meaning.

Preferably, the substituted or unsubstituted $[^{13}C_6]$-benzaldehyde is selected from the group consisting of $[^{13}C_6]$-benzaldehyde, $[^{13}C_6]$-piperonal and $[^{13}C_6]$-2,5-dimethoxy-4-methyl-benzaldehyde.

The first process step is preferably carried out in a nonpolar organic solvent, in particular a nonpolar aromatic solvent, in the presence of ammonium acetate and an organic amine, in particular a primary amine, most preferably methyl amine. The nitro compound III is isolated and purified using customary and known methods of organic synthesis.

In the second process step, the nitro group of the intermediate III is reduced and the olefinic double bond is hydrogenated to obtain a compound of the invention of the general formula I, wherein the variables $R^1$, $R^2$, $R^3$, $R^4$, $R^5$ and $R^6$ designate hydrogen atoms.

Preferably, the second process step is carried out in a nonpolar organic solvent, in particular a nonpolar aromatic solvent. Preferably, a strong reducing agent more preferably a metal hydride, even more preferably an aluminum hydride, and most preferably Vitride (Red-Al™ sodium bis(methoxyethoxy)aluminum hydride solution) is used as the reducing and hydrogenating agent. The compound of the invention of the general formula I can be isolated, purified and converted into its salts using customary and known methods of organic synthesis.

After the first process step and before the second process step, the olefinic double bond of the intermediate III can be reacted such that at least one of the aforementioned $R^4$, $R^5$ and $R^6$ groups of the general formula I is an organic residue other than a hydrogen atom. Preferably, such a reaction is carried out by using reagents containing the aforementioned $R^4$, $R^5$ and $R^6$ groups and at least one customary and known functional group which adds to olefinic double bonds, as for example, CH-acidic groups as used in the Michaelis addition.

After the second process step, the primary amino group of the compound of the invention can be reacted such that at least one of $R^1$ and $R^2$ is a residue other than a hydrogen atom. Preferably, such a reaction is carried out by using customary and known reagents for alkylating amino groups, which reagents contain $R^1$ and $R^2$ groups or their precursors. An example of a suitable reagent containing an $R^1$ and $R^2$ group is iodomethane. An example of a suitable reagent containing a precursor of $R^1$ and $R^2$ is ethyl formate, which reacts with the amino group to form a carbamate intermediate, which intermediate is reduced with a metal hydride, preferably an aluminium hydride and most preferably lithium aluminium hydride to form a methylamino group.

According to the use of the invention, the compounds of the invention, in particular the compounds of the invention prepared by the method of the invention, are excellently suited as standards in the chemical analysis and in metabolic studies. In particular, they are excellently suited as standards in the chemical analysis and in the metabolic studies of their corresponding non-labeled compounds. More particularly, they are excellently suited as internal standards in the quantitative chemical analysis of their corresponding non-labeled compounds. Most particularly, they are excellently suited as internal standards in the quantitative chemical analysis of their corresponding non-labeled compounds by LC-MS, GC-MS, LC-tandem MS and GC-tandem MS. Therefore, they are most excellently suited for the quantitative forensic chemical analysis of biological samples, in particular body fluids, especially urine. This way, the illicit use of hallucinogens and/or stimulants can be easily detected with a high accuracy and an excellent reproducibility.

Thus, according to the use of the invention, the following pairs of internal standards and corresponding analytes can be most advantageously used in forensic analysis:

[$^{13}C_6$]-amphetamine-amphetamine;
[$^{13}C_6$]-methamphetamine-methamphetamine;
[$^{13}C_6$]-3,4-methylenedioxyamphetamine-3,4-methylenedioxyamphetamine;
[$^{13}C_6$]-3,4-methylenedioxy-N-methylamphetamine-3,4-methylenedioxy-N-methylamphetamine;
[$^{13}C_6$]-macromerine-macromerine;
[$^{13}C_6$]-cathinone-cathinone;
[$^{13}C_6$]-cathine-cathine;
[$^{13}C_6$]-methcathinone-methcathinone;
[$^{13}C_6$]-ethcatinone-ethcatinone;
[$^{13}C_6$]-mephedrone-mephedrone;
[$^{13}C_6$]-1-(2-fluorophenyl)-2-methylaminopropan-1-one-1-(2-fluorophenyl)-2-methylaminopropan-1-one;
[$^{13}C_6$]-1-(3-fluorophenyl)-2-methylaminopropan-1-one-1-(3-fluorophenyl)-2-methylaminopropan-1-one:
[$^{13}C_6$]-1-(4-fluorophenyl)-2-methylaminopropan-1-one-1-(4-fluorophenyl)-2-methylaminopropan-1-one:
[$^{13}C_6$]-2,5-dimethoxy-4-methylamphetamine 2,5-dimethoxy-4-methylamphetamine;
[$^{13}C_6$]-2-methylamphetamine-2-methylamphetamine;
[$^{13}C_6$]-3-methylamphetamine-3-methylamphetamine;
[$^{13}C_6$]-4-methylamphetamine-4-methylmethamphetamine;
[$^{13}C_6$]-2-methylmethamphetamine-2-methylmethamphetamine;
[$^{13}C_6$]-3-methylmethamphetamine-3-methylmethamphetamine;
[$^{13}C_6$]-4-methylmethamphetamine-4-methylmethamphetamine;
[$^{13}C_6$]-2-methoxylamphetamine-2-methoxylamphetamine;
[$^{13}C_6$]-3-methoxyamphetamine-3-methoxyamphetamine;
[$^{13}C_6$]-4-methoxyamphetamine-4-methoxyamphetamine;
[$^{13}C_6$]-2-methoxymethamphetamine-2-methoxymethamphetamine;
[$^{13}C_6$]-3-methoxymethamphetamine-3-methoxymethamphetamine;
[$^{13}C_6$]-4-methoxymethamphetamine-4-methoxymethamphetamine;
[$^{13}C_6$]-2-fluoroamphetamine-2-fluoroamphetamine;
[$^{13}C_6$]-3-fluoroamphetamine-3-fluoroamphetamine;
[$^{13}C_6$]-4-fluoroamphetamine-4-fluoroamphetamine;
[$^{13}C_6$]-2-fluoromethamphetamine-2-fluoromethamphetamine;
[$^{13}C_6$]-3-fluoromethamphetamine-3-fluoromethamphetamine;
[$^{13}C_6$]-4-fluoromethamphetamine-4-fluoromethamphetamine;
[$^{13}C_6$]-3-methoxy-4,5-methylenedioxyamphetamine-3-methoxy-4,5-methylenedioxyamphetamine;
[$^{13}C_6$]-3-methoxy-4,5-methylenedioxyamphetamine ([$^{13}C_6$]-MMDA)-3-methoxy-4,5-methylenedioxyamphetamine;
[$^{13}C_6$]-2,4,5-trimethoxyamphetamine-2,4,5-trimethoxyamphetamine;
[$^{13}C_6$]-3,4,5-trimethoxyamphetamine-3,4,5-trimethoxyamphetamine;
[$^{13}C_6$]-2,3,4-trimethoxyamphetamine-2,3,4-trimethoxyamphetamine;
[$^{13}C_6$]-2,3,5-trimethoxyamphetamine-2,3,5-trimethoxyamphetamine:
[$^{13}C_6$]-2,3,6-trimethoxyamphetamine-2,3,6-trimethoxyamphetamine;
[$^{13}C_6$]-2,4,6-trimethoxyamphetamine-2,4,6-trimethoxyamphetamine;
[$^{13}C_6$]-2,4,5-trimethoxyphenylethylamine-2,4,5-trimethoxyphenylethylamine;
[$^{13}C_6$]-3,4,5-trimethoxyphenylethylamine-3,4,5-trimethoxyphenylethylamine;
[$^{13}C_6$]-2,3,4-trimethoxyphenylethylamine-2,3,4-trimethoxyphenylethylamine;
[$^{13}C_6$]-2,3,5-trimethoxyphenylethylamine-2,3,5-trimethoxyphenylethylamine;
[$^{13}C_6$]-2,3,6-trimethoxyphenylethylamine-2,3,6-trimethoxyphenylethylamine;
[$^{13}C_6$]-2,4,6-trimethoxyphenylethylamine-2,4,6-trimethoxyphenylethylamine;
[$^{13}C_6$]-2,5-dimethoxy-4-amylamphetamine-2,5-dimethoxy-4-amylamphetamine;
[$^{13}C_6$]-2,5-dimethoxy-4-bromoamphetamine-2,5-dimethoxy-4-bromoamphetamine;
[$^{13}C_6$]-2,5-dimethoxy-4-butylamphetamine-2,5-dimethoxy-4-butylamphetamine;
[$^{13}C_6$]-2,5-dimethoxy-4-chloroamphetamine-2,5-dimethoxy-4-chloroamphetamine;
[$^{13}C_6$]-2,5-dimethoxy-4-ethylamphetamine-2,5-dimethoxy-4-ethylamphetamine
[$^{13}C_6$]-2,5-dimethoxy-4-fluoroamphetamine-2,5-dimethoxy-4-fluoroamphetamine;
[$^{13}C_6$]-2,5-dimethoxy-4-(2-fluoroethyl)-amphetamine-2,5-dimethoxy-4-(2-fluoroethyl)-amphetamine;
[$^{13}C_6$]-2,5-dimethoxy-4-iodoamphetamine-2,5-dimethoxy-4-iodoamphetamine;
[$^{13}C_6$]-2,5-dimethoxy-4-methylamphetamine-2,5-dimethoxy-4-methylamphetamine;

[$^{13}C_6$]-2,5-dimethoxy-4-nitroamphetamine-2,5-dimethoxy-4-nitroamphetamine;
[$^{13}C_6$]-2,5-dimethoxy-4-trifluoromethylamphetamine-2,5-dimethoxy-4-trifluoromethylamphetamine;
[$^{13}C_6$]-2,5-dimethoxy-4-ethoxyamphetamine-2,5-dimethoxy-4-ethoxyamphetamine; 1
[$^{13}C_6$]-2,5-dimethoxy-4-methylthioamphetamine-2,5-dimethoxy-4-methylthioamphetamine;
[$^{13}C_6$]-2,5-dimethoxy-4-ethylthioamphetamine-2,5-dimethoxy-4-ethylthioamphetamine;
[$^{13}C_6$]-2,5-dimethoxy-4-isopropylthioamphetamine-2,5-dimethoxy-4-isopropylthioamphetamine;
[$^{13}C_6$]-2,5-dimethoxy-4-phenylthioamphetamine-2,5-dimethoxy-4-phenylthioamphetamine;
[$^{13}C_6$]-2,5-dimethoxy-4-propylthioamphetamine-2,5-dimethoxy-4-propylthioamphetamine;
[$^{13}C_6$]-2,5-dimethoxy-3,4-dimethylamphetamine-2,5-dimethoxy-3,4-dimethylamphetamine;
[$^{13}C_6$]-2,5-dimethoxy-3,4-prop-1,3-ylenamphetamine-2,5-dimethoxy-3,4-prop-1,3-ylenamphetamine;
[$^{13}C_6$]-2,5-dimethoxy-3,4-but-1,4-ylenamphetamine-2,5-dimethoxy-3,4-butl1,4-ylenamphetamine;
[$^{13}C_6$]-2,5-dimethoxy-3-isopropyoxyamphetamine-2,5-dimethoxy-3-isopropyoxyamphetamine;
[$^{13}C_6$]-2,5-dimethoxy-3-propylamphetamine-2,5-dimethoxy-3-propylamphetamine;
[$^{13}C_6$]-2,5-dimethoxy-methylselenoamphetamine-2,5-dimethoxy-methylselenoamphetamine;
[$^{13}C_6$]-2,5-dimethoxy-propylthioamphetamine-2,5-dimethoxy-propylthioamphetamine;
[$^{13}C_6$]-2,5-dimethoxy-3-cyclopropylmethylthioamphetamine-2,5-dimethoxy-3-cyclopropylmethylthioamphetamine;
[$^{13}C_6$]-2,5-dimethoxy-3-n-butylthioamphetamine-2,5-dimethoxy-3-n-butylthioamphetamine;
[$^{13}C_6$]-2,5-dimethoxy-3-(2-methoxyeth-1-yl)thioamphetamine-2,5-dimethoxy-3-(2-methoxyeth-1-yl)thioamphetamine;
[$^{13}C_6$]-2,5-dimethoxy-3-cyclopropylthioamphetamine-2,5-dimethoxy-3-cyclopropylthioamphetamine;
[$^{13}C_6$]-2,5-dimethoxy-3-(1-methyl-prop-1-yl)thioamphetamine-2,5-dimethoxy-3-(1-methyl-prop-1-yl)thioamphetamine;
[$^{13}C_6$]-2,5-dimethoxy-3-(2-fluoroeth-1-yl)thioamphetamine-2,5-dimethoxy-3-(2-fluoroeth-1-yl)thioamphetamine;
[$^{13}C_6$]-1-amino-2-(1,4-naphth-2-yl)ethane-1-amino-2-(1,4-naphth-2-yl)ethane;
[$^{13}C_6$]-3,6-dimethoxy-5-ethylthioamphetamine-3,6-dimethoxy-5-ethylthioamphetamine
[$^{13}C_6$]-2-(4-bromo-2,5-dimethoxyphenyl)ethanamine-2-(4-bromo-2,5-dimethoxyphenyl)ethanamine;
[$^{13}C_6$]-1-(4-chloro-2,5-dimethoxyphenyl)-2-aminoethane-1-(4-chloro-2,5-dimethoxyphenyl)-2-aminoethane;
[$^{13}C_6$]-1-(2,5-dimethoxy-4-methylphenyl)-2-aminoethane-(2,5-dimethoxy-4-methylphenyl)-2-aminoethane;
[$^{13}C_6$]-1-(2,5-dimethoxy-4-ethylphenyl)-2-aminoethane-1-(2,5-dimethoxy-4-ethylphenyl)-2-aminoethane;
[$^{13}C_6$]-2-(4-fluoro-2,5-dimethoxyphenyl)-1-aminoethane-2-(4-fluoro-2,5-dimethoxyphenyl)-1-aminoethane;
[$^{13}C_6$]-3,4-dimethyl-2,5-dimethoxyphenethylamine-3,4-dimethyl-2,5-dimethoxyphenethylamine;
[$^{13}C_6$]-5-(2-aminoethyl)-4,7-dimethoxyindane-5-(2-aminoethyl)-4,7-dimethoxyindane;
[$^{13}C_6$]-1,2,3,4-tetrahydro-5,8-dimethoxy-1,4-methanonaphthalene-6-ethanamine-1,2,3,4-tetrahydro-5,8-dimethoxy-1,4-methanonaphthalene-6-ethanamine

[$^{13}C_6$]-1,4-dimethoxy-2-naphthaleneethanamine-1,4-dimethoxy-2-naphthaleneethanamine:
[$^{13}C_6$]-2-(2,5-dimethoxyphenyl)ethanamine-2-(2,5-dimethoxyphenyl)ethanamine;
[$^{13}C_6$]-2,5-dimethoxy-4-iodophenethylamine-2,5-dimethoxy-4-iodophenethylamine;
[$^{13}C_6$]-2,5-dimethoxy-4-nitrophenethylamine-2,5-dimethoxy-4-nitrophenethylamine;
[$^{13}C_6$]-2-(2,4,5-trimethoxyphenyl)ethanamine-2-(2,4,5-trimethoxyphenyl)ethanamine;
[$^{13}C_6$]-2-(4-isopropoxy-2,5-dimethoxyphenyl)ethanamine-2-(4-isopropoxy-2,5-dimethoxyphenyl)ethanamine;
[$^{13}C_6$]-2-(2,5-dimethoxy-4-propylphenyl)ethanamine-2-(2,5-dimethoxy-4-propylphenyl)ethanamine;
[$^{13}C_6$]-2-(2,5-dimethoxy-4-(methylthio)phenyl)ethanamine-2-(2,5-dimethoxy-4-(methylthio)phenyl)ethanamine;
[$^{13}C_6$]-2-[4-(ethylthio)-2,5-dimethoxyphenyl]ethanamine-2-[4-(ethylthio)-2,5-dimethoxyphenyl]ethanamine;
[$^{13}C_6$]-2-[4-(Isopropylthio)-2,5-dimethoxyphenyl]ethanamine-2-[4-(Isopropylthio)-2,5-dimethoxyphenyl]ethanamine;
[$^{13}C_6$]-2-[2,5-dimethoxy-4-(propylthio)phenyl]ethanamine-2-[2,5-dimethoxy-4-(propylthio)phenyl]ethanamine;
[$^{13}C_6$]-2-[4-[(cyclopropylmethyl)thio]-2,5-dimethoxyphenyl]ethanamine-2-[4[(cyclopropylmethyl)thio]-2,5-dimethoxyphenyl]ethanamine;
[$^{13}C_6$]-2-[4-(butylthio)-2,5-dimethoxyphenyl]ethanamine-2-[4-(butylthio)-2,5-dimethoxyphenyl]ethanamine;
[$^{13}C_6$]-2-[4-(methoxyethylthio)-2,5-dimethoxyphenyl]ethanamine-2-[4-(methoxyethylthio)-2,5-dimethoxyphenyl]ethanamine;
[$^{13}C_6$]-2-[4-(cyclopropylthio)-2,5-dimethoxyphenyl]ethanamine-2-[4-(cyclopropylthio)-2,5-dimethoxyphenyl]ethanamine;
[$^{13}C_6$]-2-[4-(isobutylthio)-2,5-dimethoxyphenyl]ethanamine-2-[4-(isobutylthio)-2,5-dimethoxyphenyl]ethanamine;
[$^{13}C_6$]-2-[2,5-dimethoxy-4-(2-fluoroethylthio)phenyl]ethanamine-2-[2,5-dimethoxy-4-(2-fluoroethylthio)phenyl]ethanamine;
[$^{13}C_6$]-2,5-dimethoxy-4-(trifluoromethyl)phenethylamine-2,5-dimethoxy-4-(trifluoromethyl)phenethylamine;
[$^{13}C_6$]-4-methylaminorex-4-methylaminorex,
[$^{13}C_6$]-aminorex-aminorex; and
[$^{13}C_6$]-2,5-dimethoxy-3,4-methylenedioxyamphethamine-2,5-dimethoxy-3,4-methylenedioxyamphethamine.

EXAMPLES

Example 1

The Synthesis of DL-[$^{13}C_6$]-Amphetamine 1.1 The Synthesis of 2-Nitro-1-propene-1-yl-[$^{13}C_6$]-benzene

[$^{13}C_6$]-benzaldehyde (1.0 g, 8.92 mmol) was added to nitroethane (5 mL) in a 20 mL round bottom beaker with a magnetic stirrer. Anhydrous ammonium acetate (0.16 g, 2.1 mmol) was added and the solution was warmed to 80° C. before methyl amine (33% in ethanol, 0.1 mL) was added in one portion. The reaction was monitored by thin layer chromatography (TLC) with silica on alumina with toluene as the mobile phase. After 2 hours the reaction was complete as confirmed by GC-MS. The solvent from the reaction mixture was evaporated with reduced pressure on a rotary evaporator. The crude product was recrystallized in the beaker by addition of isopropanol (3 mL) and heating until everything was dissolved in the solvent. After slowly cooling to 4° C. over night, the crystals were separated on a Buchner funnel and washed with a small amount of cold isopropanol. The light yellow crystals obtained were dried thoroughly to remove all of the alcohol and other traces of volatile matter. They yield of 2-nitro-1-propene-1-yl-[$^{13}C_6$]-benzene was 1.1 g (6.508 mmol) corresponding to 72.9% based on [$^{13}C_6$]-benzaldehyde.

1.2 The Synthesis of DL-2-[$^{13}C_6$]-benzeneethaneamine sulfate salt 2-nitro-1-propene-1-yl-[$^{13}C_6$]-benzene (1.1 g, 6.504 mmol) was dissolved in dry toluene (20 mL). The resulting solution was added dropwise to a mixture of Vitride (Red-Al™ sodium bis(methoxyethoxy)aluminum hydride solution, 70% in toluene, 5 mL) and dry toluene (22.5 mL) at 70° C. After all the nitrostyrene solution was added, the resulting reaction mixture was stirred for 2 hours under an inert atmosphere. The reaction mixture was left over night at room temperature for the completion of the reaction. 5% by weight sodium hydroxide in water (50 mL) was then added carefully, and the toluene layer was separated. The water phase was washed with toluene (2 times 25 mL), and the organic phases were combined and washed with saturated sodium hydrogen carbonate and brine and dried with anhydrous magnesium sulfate. The solvent was evaporated to yield 930 mg of the free base as a light yellow oil. This oil was distilled on a Kiugelrohr apparatus and dissolved in anhydrous diethyl ether (20 mL).

The sulfate salt was made by a slow addition of 10% by weight concentrated sulfuric acid in diethyl ether until the pH was 4.5. The salt was separated from the solvent by filtration with a dry Buchner funnel and the product was washed by of chilled diethyl ether (2×10 mL). The salt was dried under reduced pressure to yielded 751 mg of the product corresponding to 48% based on the nitrostyrene with a purity above 99% as determined by its trifluoroacetic acid (TFAA) derivative on GC-MS.

DL-[$^{13}C_6$]-amphetamine was excellently suited as internal standard in the quantitative analysis of amphetamine by GC-tandem MS and LC-tandem MS. In the GC and LC separation, DL-[$^{13}C_6$]-amphetamine showed the same retention and elution behavior as amphetamine. The internal standard was particularly suitable of minimizing the effects of ion suppression caused by high analyte concentrations. Therefore, the quantitative analysis of amphetamine in various biological samples, such as urine, was particularly accurate and reproducible.

Example 2

The Synthesis of DL-[$^{13}C_6$]-Methamphetamine and Its Chloride Salt

Amphetamine free base (100 mg, 0.71 mmol) was dissolved in ethyl formate (10 mL). The solution was heated under pressure in an ACE pressure reactor for 2 hours at 100° C. The reaction mixture was cooled down, and the solvent was evaporated under reduced pressure. The resulting carbamate derivative was dissolved in dried diethyl ether (5 mL). The solution was added dropwise to a suspension of lithium aluminium hydride (40.4 mg, 1.07 mmol) in diethyl ether (10 mL). The mixture was refluxed for 5 hours. Thereafter, water was carefully added after the reaction mixture had been cooled down to 0° C. on an ice bath. The lithium salt was filtered over Celite™ diatomaceous earth in Buchner funnel. The granules obtained were washed thoroughly with excess diethyl ether. The combined ether phases were washed with 5% sodium hydroxide and brine before being dried with magnesium sulfate. The solvent was evaporated to yield 96 mg methamphetamine free base.

The free base was redissolved in diethyl ether. The solution was cooled down to 10° C. before HCl dissolves in isopropanol (1.85 mL) was added in small portions onto the pH reached 4. The resulting chloride salt was filtered off with a Buchner funnel, washed with diethyl ether and dried to yield to 110 mg of the product with a purity >98.8% as determined by TFAA. derivatization on GC-MS.

DL-[$^{13}C_6$]-methamphetamine was excellently suited as internal standard in the quantitative analysis of methamphetamine by GC-tandem MS and LC-tandem MS. In the GC and LC separation, DL-[$^{13}C_6$]-methamphetamine showed the same retention and elution behavior as methamphetamine. The internal standard was particularly suitable of minimizing the effects of ion suppression caused by high analyte concentrations. Therefore, the quantitative analysis of methamphetamine in various biological samples, such as urine, was particularly accurate and reproducible.

Example 3

The synthesis of DL-[$^{13}C_6$]-3,4-methylenedioxy-amphetamine

3.1 The Synthesis of 3,4-Methylenedioxy-[$^{13}C_6$]-benzene

To a stirred suspension of sodium hydride (1.25 g, 52 mmol) in hexamethylphosphoric acid triamide (HMPT, 15 mL), a solution of 1,2-dihydroxy-[$^{13}C_6$]-benzene (2.86 g, 26 mmol) in HMPT (20 mL) was added dropwise under an argon atmosphere. After the effervescence stopped, diiodomethane (8 g, 30 mmol) was added, and the resulting solution was stirred for 20 minutes. The reaction was quenched by ice water and then extracted with diethyl ether. The combined ether extracts were dried over magnesium sulfate. The diethyl ether was evaporated. The yield of 3,4-methylenedioxy-[$^{13}C_6$]-benzene was 2.9 g corresponding to 92% based on 1,2-dihydroxy-[$^{13}C_6$]-benzene.

3.2 The Synthesis of 3,4-Methylenedioxy-[$^{13}C_6$]-1-bromobenzene 3,4-methylenedioxy-[$^{13}C_6$]-benzene (1.5 g, 11.7 mmol) was dissolved in chloroform (20 mL). N-bromosuccinimide (2.16 g, 12.1 mmol) was added in small portions with intensive magnetics stirring. The reaction mixture was refluxed for 2 hours. The obtained solids were removed by filtration and washed with two small portions of cold chloroform. The combined organic fractions were evaporated, and ether (150 mL) was added before washing with water (100 mL). The organic phase was purified by dry flash on a plug of silica in a Buchner funnel using ether as the mobile phase. The yield of 3,4-methylenedioxy-[$^{13}C_6$]-1-bromobenzene was 2.17 g corresponding to 89% based on methylenedioxy-[$^{13}C_6$]-benzene.

3.3 The Synthesis of 3,4-Methylenedioxy-[$^{13}C_6$]-benzaldehyde ([$^{13}C_6$]-Piperonaldehyde)

Dried magnesium shavings (0.26 g, 10.7 mmol) and anhydrous THF (10 mL) were added to a dry two neck round bottom flask. 3,4-Methylenedioxy-[$^{13}C_6$]-1-bromobenzene (2.17 g, 10.5 mmol) was dissolved in THF (5 mL) and poured into a dropping funnel. A couple of drops of the bromide were added to the magnesium suspension and the reaction was started by the adding a few drops of dibromoethane. After the reaction started the rest of the bromide was added slowly in order for the temperature not to exceed much above 55° C. This temperature was maintained for 1 hour.

The Grignard reagent was used immediately by adding it slowly via a cannula under argon to N-methylformanilide to (2.8 g, 21 mmol) at −20° C. This temperature was kept for 0.5 hours. After reaching room temperature and stirring overnight 10 M $H_2SO_4$ (10 mL) was added together with crushed ice (20 g) to hydrolyze the imine. The suspension was extracted with diethylether and the organic phase was washed with brine (100 mL), dried over $MgSO_4$ and evaporated. The yield of [$^{13}C_6$]-piperonaldehyde was 1.09 g (6.93 mmol, 66% based on methylenedioxy-[$^{13}C_6$]-benzene).

3.4 The Synthesis of 2-Nitro-1-propen-1-yl-3,4-methylene-[$^{13}C_6$]-benzene

[$^{13}C_6$]-piperonaldehyde (1.0 g, 6.4 mmol) was added to nitroethane (5 mL) in a 20 ml round bottom beaker fitted with a magnetic stirrer. Anhydrous ammonium acetate (0.16 g, 2.1 mmol) was added and the solution was then warmed to 80° C. before methylamine (0.1 ml, 33% in ethanol) was added in one portion. The reaction was monitored by TLC with silica on aluminum using toluene as the mobile phase. After 2 hours the reaction was complete, which was confirmed by GC/MS. The solvent from the reaction mixture was evaporated under reduced pressure on a rotatory evaporator. The crude product was recrystallized directly in the beaker by addition of isopropanol (3 mL) and heating until the crystals were dissolved. By slow cooling to 4° C. overnight the crystals that formed were separated on a Buchner funnel and washed with a small amount of cold isopropanol. The light yellow crystals were dried thoroughly in order to get rid of all of the alcohol and traces of volatile matter. The yield of (2-nitro-1-propen-1-yl)-3,4-methylene-dioxy-[$^{13}C_6$]-benzene was 1.02 g (4.8 mmol, 75% based on [$^{13}C_6$]-piperonaldehyde).

3.5 The Synthesis of DL-[$^{13}C_6$]-3,4-Methylenedi-oxyamphetamine Hydrochloride (DL-[13C6]-MDA hydrochloride)

2-Nitro-1-propen-1-yl)-3,4-methylenedioxy-[$^{13}C_6$]-benzene (1.02 g, 4.8 mmol) was dissolved in 20 ml dry toluene (20 mL) and added dropwise to a mixture of Vitride (70% in toluene, 5 mL)) and dry toluene (22.5 mL) at 70° C. After all of the nitrostyrene was added, the solution was stirred under inert atmosphere for 2 hours. The reaction was left overnight at room temperature for completion. 5% NaOH in water (50 mL) was then added carefully, and the toluene layer was separated. The water phase was washed with toluene (2×25 mL), and the organic phases were combined and washed with saturated $NaHCO_3$ and brine and dried with anhydrous $MgSO_4$. The solvent was evaporated to yield the free base as a light yellow oil (930 mg). This oil was distilled on a Kugelrohr apparatus and dissolved in anhydrous diethyl ether (20 mL). The hydrochloride salt was formed by slow addition of a HCl saturated solution in diethyl ether until pH 5. The salt was filtered from the solvent with a dry Buchner funnel and the product was washed by adding chilled diethyl ether (2×10 mL). The product was dried under reduced pressure to yield the product (800 mg, 75%) with a purity greater than 99% by TFAA derivatization on GC/MS.

Example 4

The Synthesis of DL-[$^{13}C_6$]-3,4-Methylenedioxy-N-methylamphetamine (DL-[$^{13}C_6$]-MDMA)

D,L-[$^{13}C_6$]-MDA as a free base (100 mg, 0.54 mmol) was dissolved in ethylformate (10 mL) and heated under pressure in an ACE pressure reactor for 2 hours at 100° C. The reaction was cooled down and the solvent was evaporated under reduced pressure. The carbamate derivative was dissolved in dry diethyl ether (5 mL) and added dropwise to a suspension of $LiAlH_4$ (30.75 mg, 0.81 mmol) in diethyl ether (10 mL). The reaction mixture was refluxed for 5 hours and then water was added carefully after the temperature was cooled down to 0° C. on an ice bath. The lithium salt was filtered through celite in a Buchner funnel and the granules were washed thoroughly by excess ether. The ether phases were combined and washed with 5% NaOH and brine before drying over $MgSO_4$. The solvent was evaporated to yield the methamphetamine as a free base (96 mg). The crude product was redissolved in diethyl ether and cooled down to 10° C. before HCl dissolved in isopropanol (1.85 M) was added in small portions until the pH was 4. The salt was filtered off with a Buchner funnel, washed with ether and dried to yield D,L-[$^{13}CO_6$]-MDMA hydrochloride (110 mg, 86% based on D,L-[$^{13}C_6$]-MDA) with a purity higher than 99% as TFAA derivative by GC/MS.

DL-[$^{13}C_6$]-3,4-methylenedioxy-N-methylamphetamine was excellently suited as internal standards in the quantitative analysis of DL-3,4-methylenedioxy-N-methylamphetamine by GC-tandem MS and LC-tandem MS. In the GC and LC separation, DL-[13C6]-3,4-methylenedioxy-N-methylamphetamine showed the same retention and elution behavior as 3,4-methylenedioxy-N-methylamphetamine. The internal standard was particularly suitable of minimizing the effects of ion suppression caused by high analyte concentrations. Therefore, the quantitative analysis of 3,4-methylenedioxy-N-methylamphetamine in various biological samples, such as urine, was particularly accurate and reproducible.

What is claimed is:
1. A method for the quantitative determination of a narcotic drug in an analytical sample, wherein the method comprises:
   (1) identifying the narcotic drug to be quantitatively determined in an analytical sample;
   (2) selecting and adding to the analytical sample an internal standard selected from deuterium free, stable isotope labeled hallucinogens and/or stimulants comprising a 2-phenylethylamine-based structural unit and containing at least three $^{13}C$ isotopes in a phenyl residue of the 2-phenylethylamine based structural unit, as free base or salt thereof; and
   (3) quantitatively determining non-labeled narcotic drug in the analytical sample.
2. The method of claim 1, wherein the method is a forensic analysis of an unlabeled hallucinogen and/or stimulant containing a 2-phenylethylamine-based structural unit.
3. The method of claim 2, wherein the analytical sample contains or consist of body fluids.
4. The method of claim 1, wherein the analytical sample contains or consists of biological samples.

5. The method of claim 4, wherein the analytical sample contains or consist of body fluids.

6. The method of claim 1, wherein six $^{13}C$ isotopes are present in the phenyl residue of the 2-phenylethylamine based structural unit.

7. The method of claim 6, wherein the internal standard is selected from [$^{13}C_6$]-3,4-methylenedioxy-N-methylamphetamine, -3,4-methylenedioxyamphetamine, -3,4-methylenedioxy-N-ethylamphetamine, -4-methoxyamphetamine, -4-methoxymethamphetamine, -2-(4-bromo-2,5-dimethoxyphenyl)ethanamine, -amphetamine, -methamphetamine, -3-methoxy-4,5-methylenedioxyamphetamine, -2,5-dimethoxy-4-methylamphetamine, -macromerine, -normacromerine, -cathinone, -cathine, -methcathinone, -ethcatinone, mephedrone -(2-methylamino-1(4-methylphenyl)propan-1-one), -1-(2-fluorophenyl)-2-methylaminopropan-1-one, -1-(3-fluorophenyl)-2-methylaminopropan-1-one, -1-(4-fluorophenyl)-2-methylaminopropan-1-one, -2-methylamphetamine, -3-methylamphetamine, -4-methylamphetamine, -2-methylmethamphetamine, -3-methylmethamphetamine, -4-methylmethamphetamine, -2-methoxyamphetamine, -3-methoxyamphetamine, -2-methoxymethamphetamine, -3-methoxymethamphetamine, -2-fluoroamphethamine, -3-fluoroamphethamine, -4-fluoroamphethamine, -2-fluoromethamphethamine, -3-fluoromethamphethamine, -4-fluoromethamphethamine, -3,4,5-trimethoxy-2-methylamphetamine, -2,4,5-, -3,4,5-, -2,3,4- -2,3,5-, -2,3,6- and -2,4,6-trimethoxyamphetamine; -2,4,5-, -3,4,5-, -2,3,4- -2,3,5-, -2,3,6- and -2,4,6-trimethoxyphenylethylamine; -2,5-dimethoxy-4-amyl-, -2,5-dimethoxy-4-bromo-, -2,5-dimethoxy-4-butyl-, 2,5-dimethoxy-4-chloro-, -2,5-dimethoxy-4-ethyl-, -2,5-dimethoxy-4-fluoro-, -2,5-dimethoxy-4-(2-fluoroethyl)-, -2,5-dimethoxy-4-iodo-, -2,5-dimethoxy-4-methyl-, -2,5-dimethoxy-4-nitro-, -2,5-dimethoxy-4-trifluoromethyl-, -2,5-dimethoxy-4-ethoxy-, -2,5-dimethoxy-4-methylthio-, -2,5-dimethoxy-4-ethylthio-, -2,5-dimethoxy-4-isopropylthio-, -2,5-dimethoxy-4-phenylthio- and -2,5-dimethoxy-4-propylthioamphetamine; -2,5-dimethoxy-3,4-dimethyl-, -2,5-dimethoxy-3,4-prop-1,3-ylen-, -2,5-dimethoxy-3,4-but-1,4-ylen-, -2,5-dimethoxy-3-isopropyoxy-, -2,5-dimethoxy-3-propyl-, -2,5-dimethoxy-methylseleno-, -2,5-dimethoxy-propylthio-, -2,5-dimethoxy-3-cyclopropylmethylthio-, -2,5-dimethoxy-3-n-butylthio-, -2,5-dimethoxy-3-(2-methoxyeth-1-yl)thio-, -2,5-dimethoxy-3-cyclopropylthio-, -2,5-dimethoxy-3-(1-methylprop-1-yl)thio- and -2,5-dimethoxy-3-(2-fluoroeth-1-yl)thio amphetamine; -1-amino-2-(1,4-naphth-2-yl)ethane, -3,6-dimethoxy-5-ethylthioamphetamine, -1-(4-chloro-2,5-dimethoxyphenyl)-2-aminoethane, -1-(2,5-dimethoxy-4-methylphenyl)-2-aminoethane, -1-(2,5-dimethoxy-4-ethylphenyl)-2-aminoethane, -2-(4-fluoro-2,5-dimethoxyphenyl)-1-aminoethane, -3,4-dimethyl-2,5-dimethoxyphenethylamine, -5-(2-aminoethyl)-4,7-dimethoxyindane, -1,2,3,4-tetrahydro-5,8-dimethoxy-1,4-methanonaphthalene-6-ethanamine, -1,4-dimethoxy-2-naphthaleneethanamine, -2-(2,5-dimethoxyphenyl)ethanamine, -2,5-dimethoxy-4-iodophenethylamine, 2,5-dimethoxy-4-nitrophenethylamine, -2-(2,4,5-trimethoxyphenyl) ethanamine, -2-(4-isopropoxy-2,5-dimethoxyphenyl) ethanamine, -2-(2,5-dimethoxy-4-propylphenyl) ethanamine, -2-(2,5-dimethoxy-4-(methylthio)phenyl) ethanamine, -2-[4-(ethylthio)-2,5-dimethoxyphenyl] ethanamine, -2-[4-(isopropylthio)-2,5-dimethoxyphenyl] ethanamine, -2-[2,5-dimethoxy-4-(propylthio)phenyl] ethanamine, -2-[4-[(cyclopropylmethyl)thio]-2,5-dimethoxyphenyl]ethanamine, -2-[4-(butylthio)-2,5-dimethoxyphenyl]ethanamine, -2-[4-(methoxyethylthio)-2,5-dimethoxyphenyl]ethanamine, -2-[4-(cyclopropylthio)-2,5-dimethoxyphenyl]ethanamine, -2-[4-(isobutylthio)-2,5-dimethoxyphenyl]ethanamine, -2-[2,5-dimethoxy-4-(2-fluoroethylthio)phenyl]ethanamine, -2,5-dimethoxy-4-(trifluoromethyl)phenethylamine, -5-phenyl-2-aminooxazoline (-aminorex), -4-methyl-5-phenyl-2-aminooxazoline (-4-methylaminorex); -2,5-dimethoxy-3,4-methylenedioxyamphethamine (DMMDA).

8. The method of claim 6, wherein the internal standard is selected from [$^{13}C_6$]-3,4-methylenedioxy-N-methylamphetamine, [$^{13}C_6$]-3,4-methylenedioxy-N-ethylamphetamine, [$^{13}C_6$]-4-methoxyamphetamine, [$^{13}C_6$]-4-methoxymethamphetamine, [$^{13}C_6$]-2-(4-bromo-2,5-dimethoxyphenyl)ethanamine, [$^{13}C_6$]-amphetamine, [$^{13}C_6$]-methamphetamine, [$^{13}C_6$]-3,4-methylenedioxyamphetamine.

9. The method of claim 1, wherein the 2-phenylethylamine-based structural unit is of general formula I:

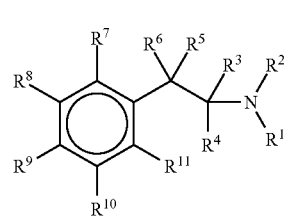

wherein:
  $R^1$, $R^2$ independently of each other, represent hydrogen atom or an organic residue selected from
    organic residues consisting of saturated or unsaturated substituted or unsubstituted alkyl, cycloalkyl, aryl, alkylcycloalkyl, alkylaryl, cycloalkylaryl or alkylcycloalkylaryl groups containing or not containing at least one heteroatom; and
    organic residues containing at least two different groups selected from saturated and unsaturated, substituted and unsubstituted alkyl, cycloalkyl, aryl, alkylcycloalkyl, alkylaryl, cycloalkylaryl and alkylcycloalkylaryl groups containing or not containing at least one heteroatom;
  $R^3$ and $R^4$ taken together represent a carbonyl oxygen atom or a substituted or unsubstituted imino group or independently of each other have the meanings given below for $R^7$ to $R^{11}$;
  $R^5$ and $R^6$ taken together represent a carbonyl oxygen atom or substituted or unsubstituted imino group or independently of each other have the meanings given below for $R^7$ to $R^{11}$;
  $R^7$ to $R^{11}$ independently of each other represent a hydrogen atom, a hydroxy group, an amino group, a mercapto group, a fluorine atom, a chlorine atom, a bromine atom, an iodine atom, a nitrile group or an organic residue selected from
    organic residues consisting of saturated or unsaturated substituted or unsubstituted alkyl, cycloalkyl, aryl, alkylcycloalkyl, alkylaryl, cycloalkylaryl or alkylcycloalkylaryl groups containing or not containing at least one heteroatom; and
    organic residues containing at least two different groups selected from saturated and unsaturated, substituted and unsubstituted alkyl, cycloalkyl, aryl, alkylcycloalkyl, alkylaryl, cycloalkylaryl and alkylcycloalkylaryl groups containing or not containing at least one heteroatom.

10. The method of claim 9, wherein at least two of $R^1$, $R^2$, $R^3$, $R^4$, $R^5$, $R^6$, $R^7$, $R^8$, $R^9$, $R^{10}$, and $R^{11}$ are bonded to each other via a bivalent bridging group.

11. The method of claim 9, wherein the deuterium free, stable isotope labeled hallucinogen and/or stimulant containing a 2-phenylethylamine-based structural unit of general formula I is prepared by a method comprising
(1) reacting [$^{13}C_6$]-benzaldehyde or a substituted [$^{13}C_6$]-benzaldehyde with a nitro group containing compound of general formula II:

to obtain a substituted or unsubstituted nitro compound of general formula III as an intermediate:

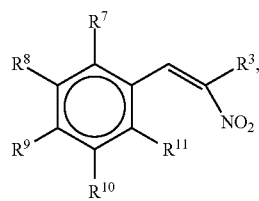

wherein $R^3$, $R^7$, $R^8$, $R^9$, $R^{10}$ and $R^{11}$ have the meanings set forth in claim 9; and
(2) reducing the $NO_2$ group and hydrogenating the olefinic double bond of the intermediate III to obtain a 2-phenylethylamine alkaloid or a psychotropic drug of general formula I, wherein $R^1$, $R^2$, $R^4$, $R^5$ and $R^6$ are hydrogen atoms.

12. The method of claim 1, wherein the internal standard is selected from 3,4-methylenedioxy-N-methylamphetamine, 3,4-methylenedioxyamphetamine, 3,4-methylenedioxy-N-ethylamphetamine, 4-methoxyamphetamine, 4-methoxymethamphetamine, 2-(4-bromo-2,5-dimethoxyphenyl)ethanamine, amphetamine, methamphetamine, 3-methoxy-4,5-methylenedioxyamphetamine, 2,5-dimethoxy-4-methylamphetamine, macromerine, normacromerine, cathinone, cathine, methcathinone, ethcatinone, mephedrone (2-methylamino-1(4-methylphenyl)propan-1-one), 1-(2-fluorophenyl)-2-methylaminopropan-1-one, 1-(3-fluorophenyl)-2-methylaminopropan-1-one, 1-(4-fluorophenyl)-2-methylaminopropan-1-one, 2-methylamphetamine, 3-methylamphetamine, 4-methylamphetamine, 2-methylmethamphetamine, 3-methylmethamphetamine, 4-methylmethamphetamine, 2-methoxyamphetamine, 3-methoxyamphetamine, 2-methoxymethamphetamine, 3-methoxymethamphetamine, 2-fluoroamphetamine, 3-fluoroamphethamine, 4-fluoroamphethamine, 2-fluoromethamphetamine, 3-fluoromethamphethamine, 4-fluoromethamphethamine, 3,4,5-trimethoxy-2-methyl amphetamine, 2,4,5-, 3,4,5-, 2,3,4- 2,3,5-, 2,3,6- and 2,4,6-trimethoxyamphetamine; 2,4,5-, 3,4,5-, 2,3,4- 2,3,5-, 2,3,6- and 2,4,6-trimethoxyphenylethylamine; 2,5-dimethoxy-4-amyl-, 2,5-dimethoxy-4-bromo-, 2,5-dimethoxy-4-butyl-, 2,5-dimethoxy-4-chloro-, 2,5-dimethoxy-4-ethyl-, 2,5-dimethoxy-4-fluoro-, 2,5-dimethoxy-4-(2-fluoroethyl)-2,5-dimethoxy-4-iodo-, 2,5-dimethoxy-4-methyl-, 2,5-dimethoxy-4-nitro-, 2,5-dimethoxy-4-trifluoromethyl-, 2,5-dimethoxy-4-ethoxy-, 2,5-dimethoxy-4-methylthio-, 2,5-dimethoxy-4-ethylthio-, 2,5-dimethoxy-4-isopropylthio-, 2,5-dimethoxy-4-phenylthio- and 2,5-dimethoxy-4-propylthioamphetamine; 2,5-dimethoxy-3,4-dimethyl-, 2,5-dimethoxy-3,4-prop-1,3-ylen-, 2,5-dimethoxy-3,4-but-1,4-ylen, 2,5-dimethoxy-3-isopropyoxy-, 2,5-dimethoxy-3-propyl-, 2,5-dimethoxy-methylseleno-, 2,5-dimethoxy-propylthio-, 2,5-dimethoxy-3-cyclopropylmethylthio-, 2,5-dimethoxy-3-n-butylthio-, 2,5-dimethoxy-3-(2-methoxyeth-1-yl)thio-, 2,5-dimethoxy-3-cyclopropylthio-, 2,5-dimethoxy-3-(1-methyl-prop-1-yl)-thio-, and 2,5-dimethoxy-3-(2-fluoroeth-1-yl)thio amphetamine; 1-amino-2-(1,4-naphth-2-yl)ethane, 3,6-dimethoxy-5-ethylthioamphetamine, 1-(4-chloro-2,5-dimethoxyphenyl)-2-aminoethane, 1-(2,5-dimethoxy-4-methylphenyl)-2-aminoethane, 1-(2,5-dimethoxy-4-ethylphenyl)-2-aminoethane, 2-(4-fluoro-2,5-dimethoxyphenyl)-1-aminoethane, 3,4-dimethyl-2,5-dimethoxyphenethylamine, 5-(2-aminoethyl)-4,7-dimethoxyindane, 1,2,3,4-tetrahydro-5,8-dimethoxy-1,4-methanonaphthalene-6-ethanamine, 1,4-dimethoxy-2-naphthaleneethanamine, 2-(2,5-dimethoxyphenyl)ethanamine, 2,5-dimethoxy-4-iodophenethylamine, 2,5-dimethoxy-4-nitrophenethylamine, 2-(2,4,5-trimethoxyphenyl)ethanamine, 2-(4-isopropoxy-2,5-dimethoxyphenyl)ethanamine, 2-(2,5-dimethoxy-4-propylphenyl)ethanamine, 2-(2,5-dimethoxy-4-(methylthio)phenyl)ethanamine, 2-[4-(ethylthio)-2,5-dimethoxyphenyl]ethanamine, 2-[4-(isopropylthio)-2,5-dimethoxyphenyl]ethanamine, 2-[2,5-dimethoxy-4-(propylthio)phenyl]ethanamine, 2-[4-[(cyclopropylmethyl)thio]-2,5-dimethoxyphenyl]ethanamine, 2-[4-(butylthio)-2,5-dimethoxyphenyl]ethanamine, 2-[4-(methoxyethylthio)-2,5-dimethoxyphenyl]ethanamine, 2-[4-(cyclopropylthio)-2,5-dimethoxyphenyl]ethanamine, 2-[4-(isobutylthio)-2,5-dimethoxyphenyl]ethanamine, 2-[2,5-dimethoxy-4-(2-fluoroethylthio)phenyl]ethanamine, 2,5-dimethoxy-4-(trifluoromethyl)phenethylamine, 1-amino-2-(1,4-naphth-2-yl)amphetamine, 3,6-dimethoxy-5-ethylthioamphetamine, 4-methyl-5-phenyl-2-amino-oxazoline (4-methylaminorex); 5-phenyl-2-amino-oxazoline (aminorex), 4-methyl-5-phenyl-2-amino-oxazoline (4-methylaminorex); 2,5-dimethoxy-3,4-methylenedioxyamphethamine (DMMDA).

13. The method of claim 1, wherein at least four $^{13}C$ isotopes are present in the phenyl residue of the 2-phenylethylamine based structural unit.

14. The method of claim 1, wherein at least five $^{13}C$ isotopes are present in the phenyl residue of the 2-phenylethylamine based structural unit.

15. A method of preparing a deuterium free, stable isotope labeled hallucinogen and/or stimulant containing a 2-phenylethylamine-based structural unit of general formula I:

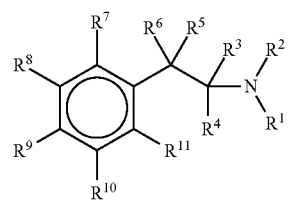

wherein:
$R^1$, $R^2$ independently of each other, represent hydrogen atom or an organic residue selected from
organic residues consisting of saturated or unsaturated substituted or unsubstituted alkyl, cycloalkyl, aryl, alkylcycloalkyl, alkylaryl, cycloalkylaryl or alkylcycloalkylaryl groups containing or not containing at least one heteroatom; and organic residues containing at least two different groups selected from saturated and unsaturated, substituted and unsubstituted alkyl, cycloalkyl, aryl, alkylcycloalkyl, alkylaryl, cycloalkylaryl and alkylcycloalkylaryl groups containing or not containing at least one heteroatom;

$R^3$ and $R^4$ taken together represent a carbonyl oxygen atom or a substituted or unsubstituted imino group or independently of each other have the meanings given below for $R^7$ to $R^{11}$;

$R^5$ and $R^6$ taken together represent a carbonyl oxygen atom or substituted or unsubstituted imino group or independently of each other have the meanings given below for $R^7$ to $R^{11}$;

$R^7$ to $R^{11}$ independently of each other represent a hydrogen atom, a hydroxy group, an amino group, a mercapto group, a fluorine atom, a chlorine atom, a bromine atom, an iodine atom, a nitrile group or an organic residue selected from organic residues consisting of saturated or unsaturated substituted or unsubstituted alkyl, cycloalkyl, aryl, alkylcycloalkyl, alkylaryl, cycloalkylaryl or alkylcycloalkylaryl groups containing or not containing at least one heteroatom; and organic residues containing at least two different groups selected from saturated and unsaturated, substituted and unsubstituted alkyl, cycloalkyl, aryl, alkylcycloalkyl, alkylaryl, cycloalkylaryl and alkylcycloalkylaryl groups containing or not containing at least one heteroatom;

wherein the method comprises (1) reacting [$^{13}C_6$]-benzaldehyde or a substituted [$^{13}C_6$]-benzaldehyde with a nitro group containing compound of general formula II:

$O_2N—CH_2—R^3$ (II), to obtain a substituted or unsubstituted nitro compound of general formula III as an intermediate:

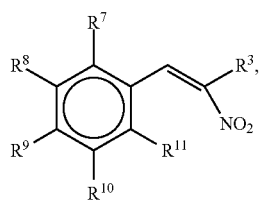

(III)

wherein $R^3$, $R^7$, $R^8$, $R^9$, $R^{10}$ and $R^{11}$ have the meanings set forth above; and (2) reducing the $NO_2$ group and hydrogenating the olefinic double bond of the intermediate of general formula III to obtain a 2-phenylethylamine alkaloid or a psychotropic drug of general formula I, wherein $R^1$, $R^2$, $R^4$, $R^5$ and $R^6$ are hydrogen atoms.

16. The method of claim 15, wherein the olefinic double bond of the intermediate of general formula III is reacted before the step (2) such that at least one of $R^4$, $R^5$ and $R^6$ in the compound of general formula I is different from a hydrogen atom.

17. The method of claim 15, wherein $R^3$ is methyl.

18. The method of claim 15, wherein the primary amino group of the compound of general formula I is reacted such that at least one of $R^1$ and $R^2$ is different from a hydrogen atom.

19. The method of claim 15, wherein the compound of general formula I is selected from [$^{13}C_6$]-3,4-methylenedioxy-N-methylamphetamine, -3,4-methylene-dioxyamphetamine, -3,4-methylenedioxy-N-ethylamphetamine, -4-methoxy-amphetamine, -4-methoxymethamphetamine, -2-(4-bromo-2,5-dimethoxyphenyl)-ethanamine, amphetamine, -methamphetamine, -3-methoxy-4,5-methylenedioxy-amphetamine, -2,5-dimethoxy-4-methylamphetamine, -macromerine, -normacromerine, -cathinone, -cathine, -methcathinone, -ethcatinone, -mephedrone, -(2-methylamino-1(4-methylphenyl)propan-1-one), -1-(2-fluorophenyl)-2-methylaminopropan-1-one, -1-(3-fluorophenyl)-2-methylaminopropan-1-one, -1-(4-fluorophenyl)-2-methylaminopropan-1-one, -2-methylamphetamine, -3-methylamphetamine, -4-methylamphetamine, 2-methylmethamphetamine, -3-methylmethamphetamine, -4-methylmethamphetamine, 2-methoxyamphetamine, 3-methoxyamphetamine, 2-methoxymethamphetamine, 3-methoxymethamphetamine, -2-fluoroamphethamine, -3-fluoroamphethamine, -4-fluoroamphethamine, -2-fluoromethamphethamine, -3-fluoromethamphethamine, 4 fluoromethamphethamine, -3,4,5-trimethoxy-2-methylamphetamine, -2,4,5-, -3,4,5-, -2,3,4-, -2,3,5-, -2,3,6- and -2,4,6-trimethoxyamphetamine; -2,4,5-, -3,4,5-, -2,3,4-, -2,3,5-, -2,3,6- and -2,4,6-trimethoxyphenylethylamine; -2,5-dimethoxy-4-amyl-, -2,5-di-methoxy-4-bromo-, -2,5-dimethoxy-4-butyl-, 2,5-dimethoxy-4-chloro-, -2,5-dimethoxy-4-ethyl-, -2,5-dimethoxy-4-fluoro-, -2,5-dimethoxy-4-(2-fluoroethyl)-, -2,5-dimethoxy-4-iodo-, -2,5-dimethoxy-4-methyl-, -2,5-dimethoxy-4-nitro-, -2,5-dimethoxy-4-trifluoromethyl-, -2,5-dimethoxy-4-ethoxy-, -2,5-dimethoxy-4-methylthio-, -2,5-dimethoxy-4-ethylthio-, -2,5-dimethoxy-4-isopropylthio-, -2,5-dimethoxy-4-phenylthio- and -2,5-dimethoxy-4-propylthioamphetamine; -2,5-dimethoxy-3,4-dimethyl-, -2,5-dimethoxy-3,4-prop-1,3-ylen-, -2,5-dimethoxy-3,4-but-1,4-ylen, -2,5-dimethoxy-3-isopropyoxy-, -2,5-dimethoxy-3-propyl-, -2,5-dimethoxy-methylseleno-, -2,5-dimethoxy-propylthio-, -2,5-dimethoxy-3-cyclopropylmethylthio-, -2,5-dimethoxy-3-n-butylthio-, -2,5-dimethoxy-3-(2-methoxyeth-1-yl)thio-, -2,5-dimethoxy-3-cyclopropylthio-, -2,5-dimethoxy-3-(1-methyl-prop-1-yl)thio- and -2,5-dimethoxy-3-(2-fluoroeth-1-yl)thio-amphetamine; -1-amino-2-(1,4-naphth-2-yl)ethane, -3,6-dimethoxy-5-ethylthio-amphetamine, -1-(4-chloro-2,5-dimethoxyphenyl)-2-aminoethane, -1-(2,5-dimethoxy-4-methylphenyl)-2-aminoethane, -1-(2,5-dimethoxy-4-ethylphenyl)-2-aminoethane, -2-(4-fluoro-2,5-dimethoxyphenyl)-1-aminoethane, -3,4-dimethyl-2,5-dimethoxy-phenethylamine, -5-(2-aminoethyl)-4,7-dimethoxyindane, -1,2,3,4-tetrahydro-5,8-dimethoxy-1,4-methanonaphthalene-6-ethanamine, -1,4-dimethoxy-2-naphthalene-ethanamine, -2-(2,5-dimethoxyphenyl) ethanamine, -2,5-dimethoxy-4-iodophenethylamine, 2,5-dimethoxy-4-nitrophenethylamine, -2-(2,4,5-trimethoxyphenyl)ethanamine, -2-(4-isopropoxy-2,5-dimethoxyphenyl)ethanamine, -2-(2,5-dimethoxy-4-propylphenyl)ethanamine, -2-(2,5-dimethoxy-4-(methylthio)phenyl)ethanamine, -2-[4-(ethylthio)-2,5-dimethoxyphenyl]ethanamine, -2-[4-(isopropylthio)-2,5-dimethoxy-phenyl]ethanamine, -2-[2,5-dimethoxy-4-(propylthio)phenyl]ethanamine, -2-[4-[(cyclopropylmethyl)thio]-2,5-dimethoxyphenyl]ethanamine, -2-[4-(butylthio)-2,5-dimethoxyphenyl]ethanamine, -2-[4-

(methoxyethylthio)-2,5-dimethoxyphenyl]-ethanamine, -2-[4-(cyclopropylthio)-2,5-dimethoxyphenyl]ethanamine, -2-[4-(isobutylthio)-2,5-dimethoxyphenyl]ethanamine, -2-[2,5-dimethoxy-4-(2-fluoro-ethylthio)phenyl]ethanamine, -2,5-dimethoxy-4-(trifluoromethyl)phenethylamine, -5-phenyl-2-amino-oxazoline (-aminorex), -4-methyl-5-phenyl-2-amino-oxazoline (-4-methylaminorex); -2,5-dimethoxy-3,4-methylenedioxyamphethamine (DMMDA).

\* \* \* \* \*